United States Patent [19]

Atkinson et al.

[11] Patent Number: 5,299,580
[45] Date of Patent: Apr. 5, 1994

[54] GUIDEWIRE WITH SAFETY RIBBON WITH SUBSTANTIALLY AXIALLY SYMMETRIC FLEXIBILITY

[75] Inventors: Robert E. Atkinson, New Brighton; Peter T. Keith, Fridley, both of Minn.

[73] Assignee: Scimed Life Systems, Inc., Maple Grove, Minn.

[21] Appl. No.: 958,953

[22] Filed: Oct. 9, 1992

[51] Int. Cl.$^5$ ............................................... A61B 5/00
[52] U.S. Cl. ................................................. 128/772
[58] Field of Search ............... 128/657, 772; 604/95, 604/164, 165, 166, 170, 171, 280, 282

[56] References Cited

U.S. PATENT DOCUMENTS

| | | | |
|---|---|---|---|
| 3,906,938 | 9/1975 | Fleischhacker | 128/2 M |
| 4,474,174 | 10/1984 | Petruzzi | 604/95 |
| 4,763,647 | 8/1988 | Gambale | 128/657 |
| 4,800,890 | 1/1989 | Cramer | 128/657 |
| 5,007,434 | 4/1991 | Doyle et al. | 128/772 |

*Primary Examiner*—Max Hindenburg
*Attorney, Agent, or Firm*—Willian Brinks Hofer Gilson & Lione

[57] ABSTRACT

A novel intravascular device is provided having a distal end including a flexible portion having an axis of elongation. The flexible portion comprises a first twist and a first flat defining a first plane, and a second twist and a second flat defining a second plane. The first plane is substantially orthogonal to the second plane for providing the distal end of the device with substantially symmetric flexibility about the axis of elongation. A novel method of manufacturing a safety ribbon for an intravascular device is also provided. The method comprises the steps of: providing an intravascular device having a substantially rounded core wire at a distal end of the device; flattening the core wire to form a substantially rectangular configuration; fixing one end of the configuration against rotation; and rotating an opposite end of the configuration with respect to the one end, thereby substantially permanently altering the configuration. Alternatively, the method can comprise the steps of: providing an element having a substantially rounded configuration; flattening the element to form a substantially rectangular configuration; providing a coil for operative attachment to the rectangular configuration; twisting the coil so as to place the coil under torsion; maintaining the coil in a torsioned condition; operatively attaching the coil to the rectangular configuration; and effectively releasing the coil such that the coil relaxes, thereby allowing torsion on the coil to twist the rectangular configuration to permanently alter the rectangular configuration.

20 Claims, 1 Drawing Sheet

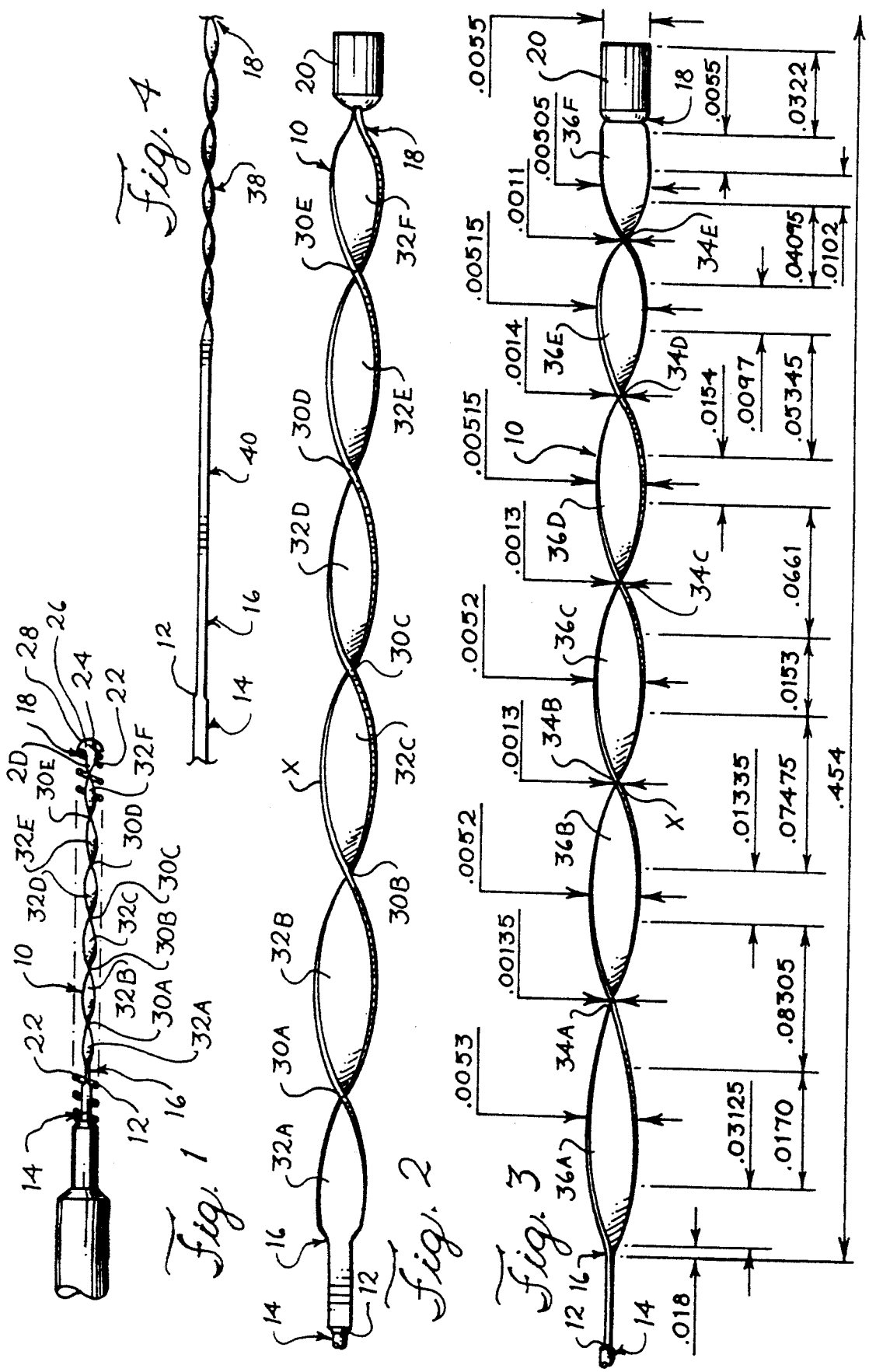

GUIDEWIRE WITH SAFETY RIBBON WITH SUBSTANTIALLY AXIALLY SYMMETRIC FLEXIBILITY

BACKGROUND OF THE INVENTION

The present invention generally relates to a novel construction for a safety ribbon or core wire. More specifically, the invention relates to a novel safety ribbon for use with a medical guidewire, or a core wire for use with a fixed wire catheter, and the like, which provides substantially symmetric flexibility of the ribbon about an axis of elongation of the ribbon and efficient response to proximally applied forces. Novel methods of manufacturing such a safety ribbon are also provided.

A safety ribbon or core wire is commonly included on the distal end of a medical guidewire or a fixed wire catheter insertable intravascularly into a patient. Such a medical guidewire or catheter has a relatively flexible distal end usually comprising a coiled member for facilitating navigation within the patient's vascular system. A distal end tip, which can be formed by a suitable welding process, for example, is often formed or disposed on the distal end of the coiled member.

As the guidewire or catheter is advanced within a vascular lumen, a juncture of multiple lumens may be encountered, or the vascular lumen may bend or curve within the patient's vasculature. As the guidewire approaches such a juncture or curve, the guidewire must be carefully navigated by a treating physician, clinician, or other medical professional, towards the vascular treatment site. The physician navigates the guidewire by applying forces to a proximal end of the wire which is disposed outside of the patient. These proximally applied forces can be directed for causing rotational, axial, or other desired intravascular movement of the guidewire.

The proximally applied forces are transmitted along the axial length of the guidewire or catheter and are intended to direct or influence the distal end thereof in the desired direction towards the treatment site. This intravascular navigation can become quite difficult and tedious, especially upon consideration of the fact that the guidewire or catheter is inserted into the patient's vascular system at a location, such as the groin, located a significant vascular distance from the treatment site, such as in a coronary or carotid artery. The probability that the distal end will have to be navigated around an increasing number of bends or curves may increase proportionally with the vascular distance between the insertion site and the treatment site.

In an effort to facilitate the navigation of the guidewire or catheter within the vascular lumen, the treating physician often bends or otherwise forms the distal end of the guidewire, specifically the coiled member and possibly the distal end tip, into a predetermined configuration prior to intravascular insertion of the distal end into the patient. The predetermined configuration is usually "J"-shaped, which can facilitate navigation of the distal end of the guidewire in the direction indicated by the distal end of the "J." The "J"-shaped configuration of the distal end can also facilitate selection of a desired branch lumen or vessel. In order to select a desired branch lumen, the treating physician applies a rotational force to the out-of-body proximal end of the guidewire. This force is transmitted along the axial length of the guidewire or core wire to induce rotation of the distal end thereof. The distal end is rotated to point the distal end of the "J" towards or into the desired branch lumen or around the curve or bend. Once the distal end of the "J" is pointed in the desired direction, axially directed forces can be applied to the proximal end to cause axial shifting of the guidewire in the desired direction. Similar navigation procedures are often employed in directing the guidewire or core wire around a sharp bend.

The formation of the coiled member and the end tip, combined with forces exerted thereon during navigation thereof through the patient's vascular system towards the treatment site can stress or otherwise weaken the distal end. In some instances, the resultant stress may be of sufficient magnitude to cause the end tip, the coiled member, or portions thereof to break away from the associated remainder of the guidewire or catheter.

In an effort to reduce the possibility that a portion of the distal end of a guidewire or a fixed wire catheter might break away therefrom, a safety wire or ribbon may be provided. The safety wire is intended to reduce the likelihood of separation of the distal end tip and portions of the coiled member from the guidewire or catheter when breakage occurs during intravascular use. Specifically, the safety wire may be operatively fixedly attached to the end tip, portions of the coiled member, and/or to the remainder of the guidewire or catheter, thereby preventing separation of those elements.

The general construction of a conventional safety wire is well known to those having ordinary skill in the relevant art. Generally, the safety wire comprises a usually flattened, planar distal segment, or element, having a substantially rectangular latitudinal cross section. Round safety wires, can be used, but may be unpopular because they resist bending into a predetermined configuration prior to intravascular insertion, which may be necessary or desirable for navigating the associated device remainder intravascularly as described earlier. In addition, a round safety wire, of a given tensile strength, can be stiffer than a flattened safety wire of similar tensile strength, which may limit the overall flexibility of round safety wire.

An example of a conventional safety wire having a flattened configuration or profile is the device disclosed in the U.S. Pat. No. 3,906,938 to Fleischhacker. Another example of a flattened safety wire, indicated by reference numeral 38 in the disclosure, is shown in the U.S. Pat. No. 5,007,434 to Doyle et al. disposed radially offset from a twisted, elongate shaft of a guidewire. In some constructions, the core wire itself is usually substantially cylindrical in configuration, and a tapered or reduced diameter distal-most segment thereof can be stamped or otherwise flattened to form the safety wire. Other methods of safety wire formation can also be used. The flattened configuration of the safety wire provides the same tensile strength as a round safety wire of equal mass and provides increased flexibility, but the flattened configuration is not as responsive to proximally applied forces as a round configuration, as will be discussed in greater detail shortly.

Opposite ends of the safety wire can be joined to a core wire and the end tip, respectively, by suitable means, such as solder and the like. In some constructions, the end tip may be formed as a part of the safety wire prior to stamping thereof. These constructions allow the distal end of the guidewire or fixed wire catheter to be formed into a predetermined configuration, as described above, relatively easily within a plane orthogonal to a plane defined by the flattened safety wire. However, it is difficult to form the distal end of the guidewire within the plane of the safety wire. In addition, it has been discovered that, irrespective of the plane in which the distal end of the guidewire or core wire is bent or formed, the planar construction of the safety wire tends to orient the bend into the plane orthogonal to the plane of the safety wire (i.e. the plane orthogonal to the plane of the wire is the preferred plane of safety wire or core wire formation). This may be undesirable in some cases, and may complicate navigation of the guidewire or fixed wire catheter within the vascular lumen, as well as limit the intravascular device's ability to select a desired branch lumen because the safety wire is not symmetrically flexible about an axis of elongation of the associated wire and does not efficiently respond to proximally applied navigation forces.

Furthermore, the presence of a limited flexibility safety ribbon in the distal end of a guidewire or of a core wire of a fixed wire catheter may limit performance of the guidewire or the catheter itself. The decreased responsiveness of the distal end to the navigating forces proximally applied by the treating physician may complicate the treatment. The lack of symmetric flexibility and efficient responsiveness of the distal end of the guidewire due to the presence of the safety wire may cause the distal end to "whip" responsive to the combination of forces applied to the proximal end of the guidewire in a navigation effort. It is believed that whipping of the distal end may be caused, or at least magnified by the non-axially symmetric flexibility of the safety wire and, consequentially, the distal end.

Illustrating the phenomenon of whipping of the distal end by example, the guidewire is intravascularly inserted into the patient. As the guidewire moves axially within the vascular lumen, the outer surface of the guidewire contacts the interior surface of the vascular lumen. Multiple bends and/or curves in the lumen can increase the contact between the guidewire and the interior surface of the vascular lumen. The contact generates a resultant force on the guidewire which can attenuate or oppose the proximally applied navigation forces, thereby inhibiting intravascular navigation of the guidewire.

Once the resultant force has achieved sufficient magnitude, the distal end does not move fully responsive to the proximally applied forces because of the attenuation of those forces by the contact-generated friction between the wire and the vascular lumen interior surface. For example, it has been empirically determined by experiment that a ninety degree rotation of the proximal end of a guidewire having a conventional safety ribbon may only result in a ten degree intravascular rotation of the distal end of the guidewire. This is an example of inefficient responsiveness of a distal end to proximally applied forces. In order to navigate the guidewire in the desired direction towards the intravascular treatment site, the treating physician applies increasingly more force (i.e. increasing degrees of rotation) to the proximal end in an effort to overcome the resultant force and to direct the distal end of the guidewire as intended.

If the proximally applied forces achieve a sufficient magnitude, that is, sufficient to overcome a static coefficient of friction between the relevant length of the guidewire and the contacted portion of the vascular lumen interior surface, the distal end whips around, or moves in response to the combined effects of the proximally applied forces. This motion is similar to the release of a wound spring. This whipping is undesirable, may make certain treatment sites difficult to reach, may complicate the procedure the physician is attempting to perform, and may be traumatic to the particular portion of the vascular lumen adjacent the whipping distal end. Similar whipping may occur with the distal end of a fixed wire catheter and other devices, and may also occur when a guidewire is rotated in a lumen within a catheter, or atherectomy device, for example.

The present invention provides a novel safety ribbon or core wire construction which is intended to solve some, if not all of the problems presented by the prior art safety ribbons or wires. Specifically, the novel construction of the safety ribbon can reduce the adverse effects of whipping while increasing navigation-facilitating flexibility and responsiveness to proximally applied forces of the distal end of a guidewire, a fixed wire catheter, and the like. A novel method of manufacturing safety ribbons is also provided.

SUMMARY OF THE INVENTION

A general object of the present invention is to provide a novel safety ribbon or core wire for intravascular use.

A more specific object of the invention is to provide a novel safety ribbon construction that can be employed within a guidewire, a core wire within a fixed wire catheter, or other suitable device.

Another object of the present invention is to provide a novel safety ribbon which provides an intravascular device with increased responsiveness to proximally applied forces or ribbons as compared to other, currently available safety wires or ribbons.

An additional object of the invention is to provide a novel safety ribbon which has increased intravascular selectability, navigability or steerability as compared to prior art safety wires or ribbons.

A further object of the present invention is to provide a novel safety ribbon which experiences less whipping than some currently available safety wires or ribbons.

Another object of the invention is to provide a novel safety ribbon having substantially symmetric flexibility about an axis of elongation of the ribbon.

An additional object of the present invention is to provide a novel safety ribbon having particular utility with intravascularly accessing coronary arteries.

A further object of the invention is to provide a novel safety ribbon having particular utility with percutaneous transluminal coronary angioplasty (hereinafter "PTCA") procedures and/or peripheral or percutaneous transluminal angioplasty (hereinafter "PTA").

Yet another object of the present invention is to provide a novel safety ribbon or core wire that reduces whipping thereof without substantially reducing the flexibility, selectability, formability or bendability, and navigability thereof.

A further object of the invention is to provide a novel safety ribbon which maintains net flexibility and tensile strength while reducing whipping.

An additional object of the present invention is to provide a novel safety ribbon including a reduced latitudinal cross section segment in a given plane for providing flexibility of the safety ribbon within that plane.

Another object of the invention is to provide a novel safety ribbon including a reduced latitudinal cross section segment in a first plane, and a similar reduced latitudinal cross section segment in a second plane offset from the first plane for providing substantially symmetric flexibility of the ribbon about a line defined by the intersection of the two planes.

Yet another object of the present invention is to provide a novel method of manufacturing a safety ribbon.

A novel intravascular device, constructed according to the teachings of the present invention, is provided having a distal end including a flexible portion having an axis of elongation. The flexible portion comprises a first twist and a first flat defining a first plane, and a second twist and a second flat defining a second plane. The first plane is substantially orthogonal to the second plane for providing the distal end of the device with substantially symmetric flexibility about the axis of elongation.

Novel methods of manufacturing a safety ribbon for an intravascular device is also provided. The method comprises the steps of: providing an intravascular device having a substantially rounded core wire at a distal end of the device; flattening the core wire to form a substantially rectangular configuration; operatively fixing one end of the configuration against rotation; and rotating an opposite end of the configuration with respect to the one end, thereby substantially permanently altering the configuration. Alternatively, the method can comprise the steps of: providing an element having a substantially rounded configuration; flattening the element to form a substantially rectangular configuration; providing a coil for operative attachment to the rectangular configuration; twisting the coil so as to place the coil under torsion; maintaining the coil in a torsioned condition; operatively attaching the coil to the rectangular configuration; and effectively releasing the coil such that the coil relaxes, thereby allowing torsion on the coil to twist the rectangular configuration to permanently alter the rectangular configuration.

BRIEF DESCRIPTION OF THE DRAWINGS

The organization and manner of the structure and operation of the invention, together with further objects and advantages thereof, may best be understood by reference to the following description taken in connection with the accompanying drawings, wherein like reference numerals identify like elements in which:

FIG. 1 is a partially sectioned side elevational view of a novel construction, according to the teachings of the present invention, for a safety ribbon for a distal end of a medical guidewire, a core wire for a fixed wire catheter, and the like;

FIG. 2 is an enlarged elevational view of the safety ribbon of the invention, illustrating the novel configuration thereof;

FIG. 3 is an enlarged elevational view, taken from a location rotated ninety degrees upwardly, as viewed, from the location of FIG. 2, showing, for means of illustration only, the dimensions of certain portions of the novel safety ribbon; and FIG. 4 is an elevational view, reduced in scale compared to the illustrations of FIGS. 2 and 3, of another embodiment of the invention.

DETAILED DESCRIPTION OF PREFERRED EMBODIMENTS

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

A novel core or safety wire or ribbon 10, constructed according to the teachings of the present invention, is illustrated in FIG. 1 located at, or included as a portion of a distal end 12 of a core wire 14, only a portion of which is visible. It is to be noted that, while the safety ribbon 10 will be discussed herein with reference to its employment with an intravascular medical guidewire for clarity of understanding, the safety ribbon 10 can be employed with a plurality of intravascular medical devices, such as a fixed wire catheter and the like, without departing from the scope of the present invention. The safety ribbon 10 may be of any dimensions suitable for a particular employment thereof, and it is to be clearly understood that the dimensions shown in FIG. 3 are given merely as an illustration of one possible embodiment of the invention and to give the reader a greater understanding of the structure of the ribbon 10.

As shown in FIG. 1, the safety ribbon 10 has a proximal portion 16 fixedly attached to the distal end 12 of the core wire 14, and a distal portion 18 which terminates in a connection element preferably in the form of a heat sink segment 20 for forming a connection between the safety ribbon 10 and a coil 22, as will be discussed later. The safety ribbon 10, in some constructions, may be a unitary extension of the core wire 14, and may have a diameter, prior to flattening thereof, somewhat smaller than a corresponding diameter of an adjacent segment of the distal end 12 of the core wire 14. Providing the ribbon 10 as a unitary extension of the core wire 14 eliminates the need for separate joining means between the safety ribbon 10 and the distal end 12 of the core wire 14. Other methods, such as soldering, brazing, welding, mechanical coupling, adhesive bonding, and the like, of joining the safety ribbon 10 to the distal end 12 of the core wire 14 are also possible without departing from the scope of the invention. It is to be noted, however, that in the preferred construction, the core wire 14 is a single piece, a distal end of which is formed, as will be discussed hereinbelow, into the safety ribbon 10.

As stated before, the distal portion 18 of the safety ribbon 10 terminates in a heat sink segment 20. In the illustrated embodiment, the heat sink segment 20 has a cross sectional area larger than a corresponding cross sectional area of the safety ribbon 10. The heat sink segment 20 may be an extension of the safety ribbon 10. The heat sink segment 20 forms appropriate means for attaching the coil 22 to the safety ribbon 10, and must include sufficient mass for forming a firm juncture between the safety ribbon 10 and the coil 22, as will be discussed in greater detail later. Because the coil 22 is welded to the core wire 14 adjacent the heat sink segment 20, the heat sink segment 20 must be able to substantially absorb a portion of the welding energy applied to the coil 22 and the heat sink segment 20 in order to prevent that energy from being appreciably transferred to the safety ribbon 10. In this manner, annealing of the safety ribbon 10 is substantially prevented during welding of the heat sink segment 20 and the coil 22.

The coil 22 comprises a plurality of joined, adjacent coils, windings or loops, preferably of a metallic wire, defining an inner diameter sufficient for accepting at least the safety ribbon 10 therein. The coil 22 has a distal end 24 joined to the safety ribbon 10 by the heat sink segment 20, and a proximal end, not shown, joined to a suitable portion of the core wire 14 in well known fashion, such as by an appropriate welding or brazing procedure. The coil 22 may extend any desired length along the core wire 14, depending upon the particular employment or construction of the core wire 14.

The distal end 24 of the coil 22 is fixedly attached to the heat sink segment 20 by means of appropriate welding, brazing, or the like. Specifically, after the heat sink segment 20 is inserted within the coil 22 and positioned such that the distal end of the heat sink segment 20 is adjacent the distal end 24 of the coil 22, an energized tungsten inert gas or TIG welding element, or other suitable device, is located in proper relation to the heat sink segment 20 and the distal end 24 for welding those two elements together. The heat sink segment 20 comprises sufficient mass, as noted hereinabove, for forming a bead 26 of material joining the segment 20 to the coil 22. The bead 26 preferably is formed with a substantially rounded distal surface 28 for presenting a substantially smooth forward profile when intravascularly inserted into a patient. The coil 22 thusly surrounds or circumscribes the entire length of the safety ribbon 10.

The novel construction of the safety ribbon 10 is illustrated in FIGS. 2 and 3. The safety ribbon 10 preferably comprises a flattened or stamped distal portion of the core wire 14 having a substantially rectangular latitudinal cross section and a substantially twisted outer surface profile extending along the entire length of the safety ribbon 10. In envisioned alternative embodiments of the invention, the safety ribbon 10 may comprise a piece separate from the core wire 14 having the same twisted configuration which is then fixedly attached to the distal end 12 of the core wire 14 by appropriate means. Also, in other embodiments of the invention, the safety ribbon 10 may include at least one substantially flat segment and at least one substantially twisted segment disposed on the ribbon 10, as shown in FIG. 4, in appropriate order for giving the ribbon 10 certain characteristics which may be desirable in a given utilization of the safety ribbon 10.

The illustrated, preferred embodiment of the safety ribbon 10 is constructed in the following manner. A predetermined portion of the distal end 12 of a substantially cylindrical core wire 14 is etched or ground to reduce the diameter thereof. If the heat sink segment 20 is to be provided as part of the safety ribbon 10 and the core wire 14, a diameter of a portion of the core wire 14 located distally of the desired location of the safety ribbon 10 may not be reduced at all, or may not be reduced to the diameter of the length of the portion of the core wire 14 that is to be formed into the safety ribbon 10. In this manner, it is insured that the heat sink segment 20 will comprise sufficient mass for forming the bead 26 to join the coil 22 to the safety ribbon 10 and thus to the core wire 14.

After the diameter of the predetermined portion of the core wire 14 which is to become the safety ribbon 10 has been sufficiently reduced, that predetermined portion is stamped or otherwise flattened, thereby transforming the original, substantially circular latitudinal cross section into a substantially rectangular latitudinal cross section. The heat sink segment 20, which is located distally of the predetermined portion, is preferably not flattened. By maintaining the substantially circular latitudinal cross section of the heat sink segment 20, proper formation of the bead 26 is facilitated.

By flattening the predetermined portion in this manner, the predetermined portion and the resulting safety ribbon 10 will be preferentially flexible in a plane orthogonal to a plane defined by the flattened portion thereof, as discussed hereinabove. Also, by flattening the ribbon 10, the ribbon 10 provides as strong a support to the coil 22 and the bead 26, and as firm an attachment of the coil 22 and the bead 26 to the core wire 14 as is provided by a substantially round safety wire of equal mass, while simultaneously providing greater flexibility for facilitating intravascular navigation of the core wire 14. Thus, the likelihood that a portion of the heat sink segment 20, the coil 22 or the bead 26 will break away from the core wire 14 and the associated device remainder is reduced without inhibiting flexibility and intravascular navigability of the distal end 12 and the associated remainder.

Once the predetermined portion is flattened, the novel twisted configuration shown in the Figures can be formed. To do this, either a proximal portion 16 or a distal portion 18 of the predetermined portion is fixed against rotation. If the proximal portion 16 is fixed, it should be so at a location distally of the core wire 14, and if the distal portion 18 is fixed, it should be so at a location near the heat sink segment 20. Now, the portion 16 or 18 opposite to the fixed portion 16 or 18 is gripped by suitable force application means for imparting a torque to the predetermined portion. After the points of fixing and gripping have been set, the predetermined portion therebetween is put under tension, preferably on the order of ten grams, for facilitating permanent, inelastic deformation of the predetermined portion for facilitating formation of the novel configuration. For the sake of clarity, the remaining manufacturing steps will be discussed with the proximal portion 16 being fixed, and with the force application means gripping the distal portion 18.

The novel twisted configuration of the safety ribbon 10 will be formed on the axial length of the predetermined portion between the point of fixing and the point of gripping. It is to be noted that, in certain embodiments of the invention, the location of the point of fixing and the point of gripping can be located on the predetermined portion such that the safety ribbon 10 comprises a twisted portion 38 and a substantially linear or planar portion 40, as shown in FIG. 4. Furthermore, the points of fixing and gripping can be located such that one end of a planar portion 40 is located adjacent the distal end 12 of the core wire 14 with the opposite end adjacent an end of the twisted portion 38, or vice versa. It is preferred, however, to locate a twisted portion 38 proximally of a planar portion 40 such that the effective length of the planar portion 40 is reduced to minimize the propensity to whip while allowing the planar portion 40 to flex or bend to form a "J", as discussed hereinabove. Additionally, the points of fixing and gripping may be serially repeated along the axial length of the predetermined portion between the distal end 12 of the core wire 14 and the proximal end of the heat sink segment 20 for forming a plurality of alternating planar portions 40 and twisted portions 38 along the axial length of the predetermined portion. These alternative constructions may present a treating physician with greater ability to reach some intravascular treatment sites.

To form the twisted portion, the force application means is energized, thereby applying a torque to the axial length of the predetermined portion between the points of fixing and gripping for causing that axial length of the predetermined portion to rotate about an axis of elongation thereof. The axial length should be rotated at least four complete rotations, or one thousand four hundred forty degrees, and is preferably rotated six complete rotations, or two thousand one hundred sixty degrees to produce a configuration having the desired benefits of the safety ribbon 10. If desired, the axial length may be rotated more than six complete rotations. Also, it is envisioned that, in certain circumstances, the axial length between the points of fixing and gripping may be rotated less than four complete rotations, and may be rotated through fractions of a complete rotation without departing from the intended scope of the present invention.

As the axial length is rotated, it twists, bends or otherwise permanently inelasticly forms to create the novel twisted configuration depicted in the Figures. Once the axial length has been rotated through the desired number of rotations about its axis of elongation, the safety ribbon 10 is completed. The points of fixing and gripping, which now define the proximal and distal portions 16 and 18 of the safety ribbon 10, respectively, are released, and the safety ribbon 10 is ready for assembly with the coil 22, as described hereinabove. It is to be clearly understood that the direction of axial length rotation can be chosen such that the twists 30A-30E, 34A-34E and the flats 32A-32F, 36A-36F are directed in the same direction, or opposite from the direction of rotation or winding of the coil 22 or, if the intravascular device includes a coiled portion located proximally or distally of the proximal portion 16 of the safety ribbon 10, of that coiled portion.

Alternatively, the novel configuration of the safety ribbon 10 can be constructed in the following manner. The predetermined portion is flattened as discussed above, and is prepared to accept the coil 22. The coil 22 is pre-twisted or wound such that the coil 22 is placed under torsion, and the ends of the coil 22 are appropriately fixed such that the torsioned condition of the coil 22 is preserved. The proximal end, not shown, and the distal end 24 of the coil 22 are fixedly attached to the core wire 14 and the heat sink segment 20, respectively, by appropriate means, such as solder, weld, braze, and the like, such that the coil 22 is maintained under torsion upon application thereof to the core wire 14.

Once the coil 22 is properly fixedly attached, the coil 22 is effectively released such that the coil 22 unwinds or otherwise relaxes under the influence of the torsion stored therein. As the coil 22 relaxes, the torsion is transferred to the predetermined portion, thereby rotating or twisting the predetermined portion to form the novel substantially twisted configuration thereon. The fixed attachments between the coil 22 and the heat sink segment 20 and the core wire 14 are sufficiently strong so that the torsion in the coil 22 effectively causes the heat sink segment 20 to rotate with respect to the portion of the core wire 14 located proximally of the proximal portion 16 of the predetermined portion. Thus, the predetermined portion is effectively rotated substantially similar to the rotation produced by the first-discussed method of manufacture. The torsion applied to the coil 22 can be predetermined to produce the desired number of twists 30A-30E, 34A-34E and flats 32A-32F, 36A-36F on the safety ribbon 10. Other methods of manufacture of the safety ribbon 10 are also possible without departing from the scope of the invention.

In the illustrated embodiment, five bends or twists 30A, 30B, 30C, 30D, and 30E, visible in FIG. 2, separated by six planes or flats 32A, 32B, 32C, 32D, 32E, and 32F are formed in a first plane of the safety ribbon 10, while five bends or twists 34A, 34B, 34C, 34D, and 34E, visible in FIG. 3, separated by six planes or flats 36A, 36B, 36C, 36D, 36E, and 36F are formed in a second plane of the safety ribbon 10. The first plane is substantially orthogonal to the second plane, and the first and second planes intersect substantially along the axis of elongation of the safety ribbon 10. Also, it is to be noted that adjacent flats 32A-32F and 36A-36F are separated by twists 30A-30E and 34A-34E, respectively. Furthermore, it is to be recognized that the twists 30A-30E and 34A-34E form the reduced latitudinal cross section segments, referred to hereinabove, in their respective planes for providing flexibility of the safety ribbon 10 in those planes, while the flats 32A-32F and 36A-36F provide flexibility out of those planes.

The axial length between the points of fixing and gripping is rotated two thousand one hundred and sixty degrees, thereby forming the particular twisted structure illustrated. It is to be noted that each flat 32A-32F represents successive one hundred eighty degrees of rotation, which, in combination, accounts for one thousand eighty degrees of rotation, or half of the rotation of the axial length. However, it is to be recognized that each of the flats 36A-36F also represents successive one hundred eighty degrees of rotation, which, when combined with the degrees of rotation of the flats 32A-32F, accounts for the total rotation of the axial length.

By providing at least one flat in each of the first and second planes of the safety ribbon 10, the safety ribbon 10 has flexibility or formability that is substantially symmetric about the axis of elongation of the ribbon 10. Viewed in another way, it can be said that the provision of at least one flat in each of the first and second planes provides the safety ribbon 10 with a flexibility or bendability about the axis of elongation thereof which is less asymmetric than the corresponding flexibility of the prior art safety wires and ribbons discussed hereinabove.

Specifically, a first flat provides flexibility in two one hundred and eighty degree arcs, one arc on each side of the flat, with respect to the first plane, defined by the flat, but does not allow flexibility within the first plane of the flat. Another flat, rotatably offset from the first flat, provides similar double-sided one hundred eighty degree flexibility with respect to the second plane defined by the second flat. By combining the flexibilities provided by two flats, which are preferably offset from each other by ninety degrees, the safety ribbon 10 is capable of flexing within a full three hundred sixty degree arc about the axis of elongation of the ribbon 10, thereby giving the ribbon 10 substantially symmetric axial flexibility.

This novel aspect of the invention is illustrated in FIGS. 2 and 3. FIGS. 2 and 3 are views of the same safety ribbon 10, but taken from different angles. Specifically, the view of FIG. 3 is taken from an observation position rotated from the observation position of FIG. 2 ninety degrees upward, as viewed, with respect to the ribbon 10. The views of FIGS. 2 and 3 correspond to the first and second planes discussed above. Comparing the views of FIGS. 2 and 3, one can see that the twists 30A-30E of FIG. 2 correspond to the flats 36A-36F of FIG. 3, while the twists 34A-34E of FIG. 3 correspond to the flats 32A-32F of FIG. 2. The lack of one-to-one correspondence between the flats and the twists of the two Figures is due to the asymmetry of the juncture between the distal end 12 of the core wire 14 and the proximal portion 16 of the safety ribbon 10 in FIGS. 2 and 3.

However, it is to be noted that the point labeled "X" in FIGS. 2 and 3 is the same location on the safety ribbon 10, but viewed from different angles, or, more precisely, from different planes defined by the alternating twists and flats. Specifically, the point "X" is on the side of the flat 32C, and is thus within the first plane defined by and containing the flats 32A-32F, as shown in FIG. 2. But, FIG. 3 shows that the point "X" is also on the side of the twist 34B which is within the second plane defined by and containing the flats 36A-36F. Thus, the safety ribbon 10 is capable of flexibility in both the first and second planes, and is capable of flexing substantially symmetrically about the axis of elongation of the ribbon 10 by appropriately combining flexibilities in those two offset or orthogonal planes.

To give the reader a greater understanding of the particular configuration of the safety ribbon 10, the following example is provided. It is suggested that the reader take a rubber band having a substantially rectangular latitudinal cross section and cut it to form a strip. While firmly holding both ends of the strip, rotate one end of it while holding the opposite end fixed a sufficient number of times to form a plurality of twists on the strip. The reader's holding of an end of the strip and rotating of the opposite end thereof mimics the safety ribbon 10 construction process described hereinabove.

The reader should position the twisted strip directly in front of himself, preferably at eye level, and look straight ahead at the twisted strip and identify a particular flat. Identification of a particular flat may be facilitated by making a mark on one side only of the strip and rotating or twisting the strip such that the mark is contained on a side of a flat. This mark is akin to the point "X" in FIG. 2. It may also be helpful to position the particular flat so that it is substantially vertical at this point. With a particular flat identified, the reader should reposition himself with respect to the strip, such as by moving the strip downwardly and his head over the strip, and look straight down at the strip and specifically at the location of the identified particular flat. It is important that the reader maintain the twisted condition on the strip constant throughout performance of the example. The reader will observe, if the example is correctly performed, that the mark is still partially visible on the side of the particular flat which is now seen as a twist in a plane offset or substantially orthogonal to the first plane of observation. This is how the point "X" appears in FIG. 3.

In light of the example, it can be appreciated that the novel structure of the safety ribbon 10 can be described in a number of equally valid ways. For instance, the ribbon 10 comprises alternating twists 30A-30E and flats 32A-32F disposed along the axial length of the safety ribbon 10 in a first plane, and alternating twists 34A-E and flats 36A-F disposed along the axial length of the safety ribbon 10 in a second plane substantially orthogonal to the first plane. Alternatively, the ribbon 10 comprises alternating twists 30A-30E and flats 32A-32F defining a first plane which correspond to alternating twists 34A-34E and flats 36A-36F in a second plane offset, preferably ninety degrees from the first plane. Further, the ribbon 10 comprises alternating twists 30A-30E and flats 32A-32F in a first plane and corresponding alternating twists 34A-34E and flats 36A-36F in a second plane substantially orthogonal to the first plane with the twists 34A-34E lagging behind the flats 32A-32F and the flats 36A-36F leading the twists 30A-30E along the axial length of the ribbon 10. Also, the ribbon 10 comprises a first portion defining a first plane and a second portion defining a second plane with the first portion being flexible substantially within and offset from or substantially orthogonal to the second plane and the second plane being flexible substantially within the first plane. All of the above descriptions of the novel configuration of the safety ribbon 10 provide for and explain the substantially symmetric flexibility and more efficient responsiveness to proximally applied forces of the distal end.

Because of the presence of flats 32A-32F and 36A-36F in two offset, and preferably substantially mutually orthogonal planes, the safety ribbon 10 has substantially symmetric flexibility about an axis of elongation of the ribbon 10. This flexibility provides the safety ribbon 10, and thereby the associated device remainder, such as a medical guidewire, a fixed wire catheter, and the like, with increased steerability or navigability within a patient's vascular lumen, as compared to currently available safety wires. Specifically, because the safety ribbon 10 has substantially axially symmetric flexibility, a treating physician may have an easier time in bending the safety ribbon 10, as well as the associated distal end of the device remainder, into a desired, predetermined configuration prior to intravascular insertion thereof for facilitating intravascular navigation of the device. The flats 32A-32F and 36A-36F facilitate formation of the safety ribbon 10. Because the safety ribbon 10 does not have a preferred plane of formation, the safety ribbon 10 will not attempt to reorient any bend applied by the treating physician into a particular plane. This can increase the navigability and branch lumen selectability of the safety ribbon 10 and the intravascular device as a whole.

The twisted configuration of the safety ribbon 10 also tends to increase response thereof to proximally applied navigation forces and to decrease the tendency of the ribbon 10 and the distal end of the associated device remainder to whip responsive to such forces. By providing substantially axially symmetric flexibility, as opposed to flexibility in just one plane as provided by the safety ribbons and wires of the prior art, the safety ribbon 10 tends to respond to proximally applied forces more efficiently than the prior art devices.

To verify this comparison by experiment, wires having safety ribbons of the prior art, and other wires having the safety ribbon 10 are placed within a relatively tightly constraining, curved lumen. Specifically, it has been empirically determined by experiment, using a prior art safety ribbon lacking a twisted portion 38, a proximally applied navigation force resulting in a ninety degree rotation of the proximal end of an associated wire may result in only a ten degree intravascular rotation of the distal end thereof. Also, a two hundred seventy degree rotation of the proximal end may only result in a forty five degree intravascular rotation of the distal end. Upon further rotation of the proximal end of the associated wire, the safety ribbon and the distal end of the wire experience whipping, as discussed earlier.

Under the same conditions, utilization of the safety ribbon 10 having a preferred twisted portion 38, as described above, can produce a seventy degree intravascular rotation of the distal end responsive to ninety degree rotation of the proximal end, and a two hundred seventy degree rotation of the proximal end can produce a two hundred sixty degree intravascular rotation of the distal end. This type of proportion between proximal end rotation and resulting distal end rotation defines more efficient responsiveness to proximally applied forces. Furthermore, upon further rotation of the proximal end of the associated wire, no whipping of the safety ribbon 10 or the distal end of the wire occurs. Because the twisted portion 38 of the safety ribbon 10 reduces the effective length of the planar portion 40, the distal end is more responsive to proximally applied forces as compared to the prior art constructions, and the safety ribbon 10 can significantly reduce the tendency of the distal end to whip within a vascular lumen. This can reduce the probability of whip-induced trauma to the patient. In addition, the twisted portion 38 reduces the propensity for whipping while also not significantly reducing overall ribbon 10 flexibility and tensile strength necessary for effective intravascular navigation.

It is envisioned that the increased intravascular navigability and distal end force responsiveness provided by the safety ribbon 10 can make certain intravascular treatment sites more readily accessible than before. Thus, the safety ribbon 10 can have particular utility with PTA, PTCA and other intravascular procedures in the peripheral and coronary vasculature, for example. It is hoped that the safety ribbon 10 of the invention may facilitate intravascular treatment procedures in general.

While preferred embodiments of the present invention are shown and described, it is envisioned that those skilled in the art may devise various modifications of the present invention without departing from the spirit and scope of the appended claims.

We claim:

1. An intravascular guidewire having a flexible distal portion comprising:
   a coil; and
   a flat ribbon extending through at least a portion of said coil and connected thereto;
   said flat ribbon having a twisted geometry such that a flat side of a first section of said flat ribbon is oriented orthogonally to the flat side of a section of said flat ribbon longitudinally adjacent thereto.

2. The intravascular guide wire of claim 1 in which the flat ribbon is connected to the coil at a distal end thereof.

3. The intravascular guide wire of claim 1 in which the flat ribbon is connected to the coil at a proximal end thereof.

4. The intravascular guide wire of claim 1 in which the flat ribbon is connected to the coil at both a distal end and a distal end thereof.

5. The intravascular guide wire of claim 1 further comprising:
   an tip connected to both a distal end of the flat ribbon and a distal end of the coil.

6. The intravascular guide wire of claim 1 in which the flat ribbon is formed of deformable material.

7. The intravascular guide wire of claim 6 in which the flat ribbon is composed a material strong enough relative to the coil such that a bend imparted to the safety ribbon, such bend formed by bending the distal portion of the guide wire beyond the elastic limit of the material of the safety ribbon, causes the distal portion of the guide wire including the portion of the coil surrounding the safety ribbon to conform to said bend.

8. An intravascular guidewire comprising:
   a core wire extending from a proximal portion to a distal portion;
   a flat safety ribbon
   extending from said core wire through said distal portion, said flat safety ribbon formed of a deformable material sufficiently strong so that said flat safety ribbon can be bent beyond the elastic limit thereof to impart a desired bend shape to said distal portion of said guidewire for use;
   and further in which said deformable flat safety ribbon has a twisted orientation along at least a portion of a length thereof.

9. The intravascular guide wire of claim 8 in which the safety ribbon is composed a material strong enough such that a bend imparted to the safety ribbon, such bend formed by bending the distal portion of the guide wire beyond the elastic limit of the material of the safety ribbon, causes the distal portion of the guide wire to conform to said bend.

10. The intravascular guide wire of claim 8 further comprising:
    a coil surrounding said flat safety ribbon.

11. The intravascular guide wire of claim 10 in which the flat safety ribbon is connected to the coil at a distal end thereof.

12. The intravascular guide wire of claim 10 in which the flat safety ribbon is connected to the coil at a proximal end thereof.

13. The intravascular guide wire of claim 10 in which the flat safety ribbon is connected to the coil at both a distal end and a distal end thereof.

14. An intravascular guidewire comprising:
    a flexible distal end including:
    a coil;
    a flat deformable ribbon extending therethrough, said flat ribbon being twisted along a length thereof.

15. The intravascular guide wire of claim 14 in which the flat ribbon is connected to the coil at a distal end thereof.

16. The intravascular guide wire of claim 14 in which the flat ribbon is connected to the coil at a proximal end thereof.

17. The intravascular guide wire of claim 14 in which the flat ribbon is connected to the coil at both a distal end and a distal end thereof.

18. An intravascular guidewire comprising a flexible distal portion defining an outer surface and a flat ribbon extending through said distal portion, said flat ribbon being fixed longitudinally relative to the outer surface of said distal portion, and further in which said flat ribbon has a twisted geometry such that a flat side of a first section of said flat ribbon is oriented orthogonally to the flat side of a section of said flat ribbon located longitudinally adjacent thereto.

19. The intravascular guide wire of claim 18 in which the distal portion further comprises a coiled spring, said coiled spring defining said outer surface of said distal portion.

20. The intravascular guide wire of claim 19 in which the flat ribbon is fixed to prevent longitudinal movement relative to the coiled spring.

* * * * *

UNITED STATES PATENT AND TRADEMARK OFFICE
CERTIFICATE OF CORRECTION

PATENT NO. : 5,299,580
DATED : April 5, 1994
INVENTOR(S) : Robert E. Atkinson and
Peter T. Keith It is certified that error appears in the above-indentified patent and that said Letters Patent is hereby corrected as shown below:

In claim 4, column 13, line 54, delete "distal" and substitute --proximal-- therefor.

In claim 5, column 13, line 58, delete "an" and substitute --a-- therefor.

In claim 7, column 13, line 63, after "composed" insert --of--.

In claim 9, colum 14, line 18, after "composed" insert --of--.

In claim 13, column 14, line 35, delete "distal" and substitute --proximal-- therefor.

In claim 17, column 14, line 49, delete "distal" and substitute --proximal-- therefor.

Signed and Sealed this

Fourth Day of October, 1994

Attest:

BRUCE LEHMAN

*Attesting Officer*  *Commissioner of Patents and Trademarks*